(12) United States Patent
Bindszus et al.

(10) Patent No.: US 6,178,343 B1
(45) Date of Patent: Jan. 23, 2001

(54) PULSE RATE AND HEART RATE COINCIDENCE DETECTION FOR PULSE OXIMETRY

(75) Inventors: Andreas Bindszus, Boeblingen; Andreas Boos, Bondorf, both of (DE)

(73) Assignee: Hewlett Packard Company, Palo Alto, CA (US)

( * ) Notice: Under 35 U.S.C. 154(b), the term of this patent shall be extended for 0 days.

(21) Appl. No.: 09/315,698

(22) Filed: May 20, 1999

(30) Foreign Application Priority Data

Jun. 5, 1998 (EP) .................................................. 98110266

(51) Int. Cl.[7] ........................................................ A61B 5/00
(52) U.S. Cl. ............................ 600/323; 600/324; 600/483
(58) Field of Search ..................................... 600/323, 324, 600/333, 336, 479, 483

(56) References Cited

U.S. PATENT DOCUMENTS

| | | |
|---|---|---|
| 3,858,574 | 1/1975 | Page . |
| 4,928,692 | 5/1990 | Goodman et al. . |
| 5,123,420 | 6/1992 | Paret . |
| 5,285,784 * | 2/1994 | Secker ................................. 600/331 |
| 5,485,847 * | 1/1996 | Baker, Jr. ............................. 600/323 |
| 5,971,930 * | 10/1999 | Elghazzawi ........................... 600/483 |

\* cited by examiner

Primary Examiner—John P. Lacyk

(57) ABSTRACT

A coincidence recognition unit receives a first signal indicative of a pulse rate derived from pulse oximetry and a second signal indicative of a heart rate. A coincidence detection unit generates a third signal indicative of the coincidence between the first signal and the second signal. The pulse rate of a patient (detected by pulse oximetry) can thus be compared with the heart rate of the patient (e.g. from EKG or ultrasound). An indicator is preferably generated when the pulse rate and the heart rate do not match e.g. within a pre-given limit. A warning signal might further be generated indicating that the oxygen saturation value as measured by the pulse oximetry is not sufficiently accurate and/or invalid. A pulse oximetry unit according to the invention comprises a pulse oximeter for generating the first signal, a heart rate determination unit for generating the second signal, and the coincidence recognition unit receiving the first and second signals. The coincidence recognition unit provides the third signal indicative of the coincidence between the first and the second signal to the pulse oximeter for validating the accuracy of measured oxygen saturation values of any kind of patient such as adults, pediatrics, or neonates.

10 Claims, 1 Drawing Sheet

PULSE RATE AND HEART RATE COINCIDENCE DETECTION FOR PULSE OXIMETRY

BACKGROUND OF THE INVENTION

The present invention relates to the measuring of blood oxygen saturation, and in particular to validating the accuracy of measured oxygen saturation values.

Pulse oximetry is commonly used for measuring and displaying various arterial blood characteristics including blood oxygen saturation of hemoglobin in arterial blood, the pulse rate as the rate of blood pulsation in the arteries corresponding to the heart rate of the patient, or a perfusion indicator. Pulse oximetry represents a well-established technique in the art and needs only to be briefly discussed herein.

Pulse oximeters generally determine the arterial oxygen saturation of hemoglobin (also called SpO2 or SaO2 measurement) by way of a non-invasive technique using two different monochromatic light sources typically formed by light emitting diodes (LEDs). An example for a pulse oximeter is the Hewlett Packard Component Monitoring System with the Pulse Oximeter Module, the 'HP M1020A'.

As known in the art of pulse oximetry, the light of both light sources is attenuated by static and dynamic absorbers on its path through the patient's body to a light detector. The arterial blood whose quantity varies with the time synchronously with the patient's heartbeat represents the only dynamic absorber during the pulse period. All other absorbers, such as skin, tissue or bone, are not time-variant. Thus, pulse oximeters make use of the pulsatile component of arterial blood generated by the heartbeat at only two spectral lines.

The light detector receives the modulated light intensities of each wavelength. The signals are usually amplified, low pass filtered, converted from analog to digital and further processed. A pulse finding algorithm analyses the received signals, which are so-called spectrophotometric signals, for identifying the pulses and for determining the pulse. After identifying the pulse period, the diastolic and systolic values of the spectrophotometric signals are determined and the so-called relative absorption ratios are derived therefrom. Subsequently, in a saturation calculation algorithm the arterial oxygen saturation is computed from the relative absorption ratio using calibration data and so-called extinction coefficients from the absorption spectrum of hemoglobin and oxyhemoglobin at the appropriate wavelengths. The mathematical background therefor, which makes use of Lambert-Beer's law, has been described in sufficient detail in a multiplicity of former publications such as EP-A-262 778.

In parallel to the calculation of the oxygen saturation, the period between pulses is converted into the beat-to-beat pulse rate (rate=1/period). The beat-to-beat pulse rates are then averaged over a certain intervals or number of beats to generate a more or less stable value of the pulse rate. Typical averaging is done over 4,8 or 18 beats, or over 5 to 20 seconds.

Since the early 1980s, when pulse oximetry was introduced, this non-invasive method of monitoring the arterial oxygen saturation level in a patient's blood has become a standard method in the clinical environment because of its simple application and the high value of the information applicable to nurses and doctors. It has become as common in patient monitoring to measure the oxygen level in the blood as to monitor heart activity with the ECG. In some application areas, like anesthesia in a surgical procedure, it is mandatory for doctors to measure this vital parameter.

More background information about pulse oximetry is given e.g. by S. Kastle et al., "A New Family of Sensors for Pulse Oximetry", Hewlett-Packard Journal, February 1997, pages 39–53.

U.S. Pat. No. 4,928,692 (Goodman) discloses a method for synchronizing the sampling of a signal that is then to be processed by a pulse oximeter. The described technique acts as a filter that gates the input signal for further processing in the pulse oximeter. The method is based on the real time ECG-Signal (and only on this one) with its known QRS shape characteristic as the gating trigger.

Pulse oximetry, however, relies on the fact that the arterial blood is the only pulsating component that causes a pulsatile change of the light absorption used to determine the oxygen saturation. When the source of the pulsatile component is not the patient's arterial blood flow, the oxygen saturation measurement, however, might derive inaccurate values. In case of standard pulse oximetry (e.g. adult, pediatric, neonatal) motion artifacts can cause other non-arterial pulsating components. In case of e.g. fetal pulse oximetry using reflectance sensors, the sensor can accidentally pick up the mother's pulsating blood instead of the fetal pulsating blood and lead to a wrong value of the oxygen saturation. In general, oxygen saturation values derived by pulse oximetry might not be sufficient accurate due to a strong impact of pulsatile sources other than the patient's arterial blood flow.

It is therefore an object of the present invention to provide an improved pulse oximetry.

SUMMARY OF THE INVENTION

The object is solved by the independent claims. Preferred embodiments are given by the dependent claims.

The invention makes use of the fact that the pulse rate determined by the pulse oximetry has to be correlated—for physical reasons—to the patient's heart rate. The patients heart rate can be measured directly by applying electrodes to the skin of the patient and measure the electrical activity of the contracting heart muscle (e.g. electrocardiography—EKG). Further more, the heart rate can also be measured indirectly by listening to (e.g. acoustically monitoring) the heart beat or by measuring the Doppler-shift of an ultrasound wave reflected by the moving parts of the heart.

It is to be understood that the term 'pulse rate', as used herein, shall refer to a pulsating value determined by pulse oximetry, whereas the term 'heart rate', as used herein, shall refer to a pulsating value determined by any kind of direct (e.g. EKG) or indirect (e.g. ultrasound) heart monitoring other than pulse oximetry.

According to the invention, a coincidence recognition unit receives a first signal indicative of a pulse rate derived from pulse oximetry and a second signal indicative of a heart rate. A coincidence detection unit generates a third signal indicative of the coincidence between the first signal and the second signal. The pulse rate of a patient (detected by pulse oximetry) can thus be compared with the heart rate of the patient (e.g. from EKG or ultrasound). An indicator is preferably generated when the pulse rate and the heart rate do not match e.g. within a pre-given limit. A warning signal might further be generated indicating that the oxygen saturation value as measured by the pulse oximetry is not sufficiently accurate and/or invalid.

A pulse oximetry unit according to the invention comprises a pulse oximeter for generating the first signal, a heart rate determination unit for generating the second signal, and the coincidence recognition unit receiving the first and second signals. The coincidence recognition unit provides the third signal indicative of the coincidence between the first and the second signal to the pulse oximeter for validating the accuracy of measured oxygen saturation values. The invention thus allows validating the accuracy of measured oxygen saturation values of any kind of patient such as adults, pediatrics, or neonates.

In fetal pulse oximetry, the invention allows validating that the measured oxygen saturation comes from the fetus and not from the mother. In that context, the invention might be applied in combination with the so-called cross-channel verification method as disclosed in U.S. Pat. No. 5,123,420 by the same applicant. The cross-channel verification allows discriminating heart rates of the mother and up to two fetuses within a multi-channel fetal monitor (twin monitoring). The fetal monitor is capable of recording the heart rate trace (e.g. the beat-to-beat heart rate trace) of a fetus and a second heart rate trace of the mother or of a second fetus. Coincidence between the heart rate traces is detected by means of a direct or indirect comparison of the two traces and comparison of the difference with a predefined or adaptive limit. A warning signal is generated if coincidence is detected or, in other words, when the heart rate that should come from either the mother, the first or the second fetus is equal or similar. In this case the user will be warned that the monitor might not monitor three individual objects, but instead may duplicate one object on (an) other channel(s).

The comparison between the pulse rate and the heart rate can be accomplished by any comparison method and/or apparatuses as known in the art, and preferably, by the comparison method or means as disclosed in U.S. Pat. No. 5,123,420. Accordingly, any criteria as known in the art can be applied for determining the correlation between the pulse rate and the heart rate, or in other words, whether the pulse rate and the heart rate match. Suitable measures, such as a warning signal, might be initiated when a mismatch between the pulse rate and the heart rate is detected.

BRIEF DESCRIPTION OF THE DRAWINGS

Other objects and many of the attendant advantages of the present invention will be readily appreciated and become better understood by reference to the following detailed description when considering in connection with the accompanied drawings in which.

DETAILED DESCRIPTION OF THE INVENTION

Figure 1:
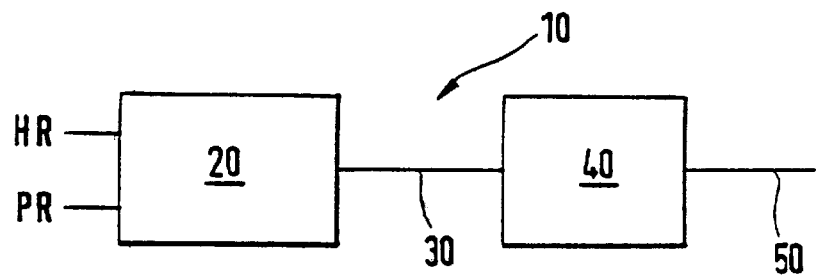
FIG. 1 shows a coincidence recognition unit according to the invention.

FIG. 1 shows in a principal block diagram a coincidence recognition unit 10 according to the invention an apparatus for providing a coincidence detection between a heart rate and a pulse rate. The coincidence recognition unit 10 comprises a coincidence detection unit 20 receiving a first signal PR indicative of the pulse rate derived from pulse oximetry and a second signal HR indicative of the heart rate measured either directly (e.g. by ECG) or indirectly (e.g. by ultrasound). The coincidence detection unit 20 generates therefrom a third signal 30 indicative of the coincidence of the first signal PR and the second signal HR. The third signal 30 is coupled to an optional coincidence evaluation unit 40 for generating a fourth signal 50, which can be a warning signal, when the third signal 30 exceeds a predefined relation to a given limit.

According to the invention, the coincidence recognition unit 10 determines whether the pulse rate and the heart rate coincide, or in other words, whether the pulse rate and the heart rate probably originate from the same patient. For that purpose, the coincidence detection unit 20 preferably determines the correlation between the pulse rate and the heart rate and the coincidence evaluation unit 40 generates the fourth signal 50 when the correlation between the pulse rate and the heart rate exceeds a given limit.

Figure 2:
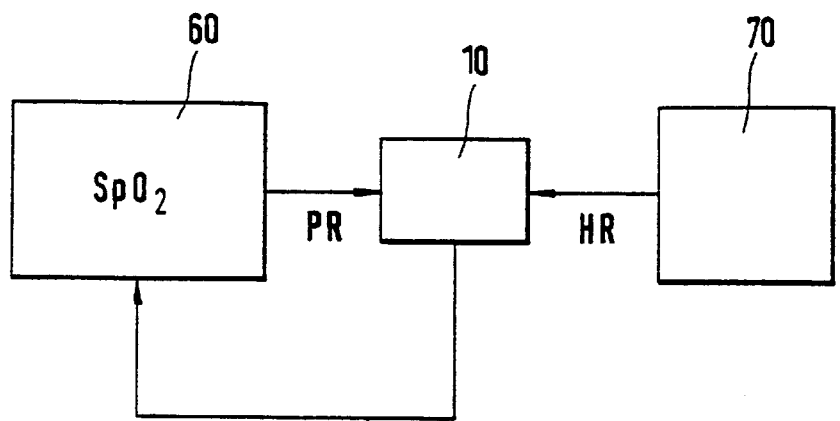
FIG. 2 shows an improved pulse oximetry unit according to the invention.

FIG. 2 shows an improved pulse oximetry unit according to the invention. A pulse oximeter 60 provides the first signal PR indicative of the pulse rate to the coincidence recognition unit 10, which further receives the second signal HR indicative of the heart rate from a heart rate determination unit 70. The heart rate determination unit 70 can be e.g. an ECG or an ultrasound-providing unit. The coincidence recognition unit 10 provides the third signal 30 and/or the fourth signal 50 to the pulse oximeter 60. The coincidence recognition unit 10 validates the accuracy of measured oxygen saturation values by determining the coincidence between the pulse rate and the heart rate. A mismatch between the pulse rate and the heart rate is signaled by the third signal 30 and/or the fourth signal 50 indicating that the oxygen saturation value as measured by the pulse oximetry is not sufficiently accurate and/or invalid.

Figure 3:
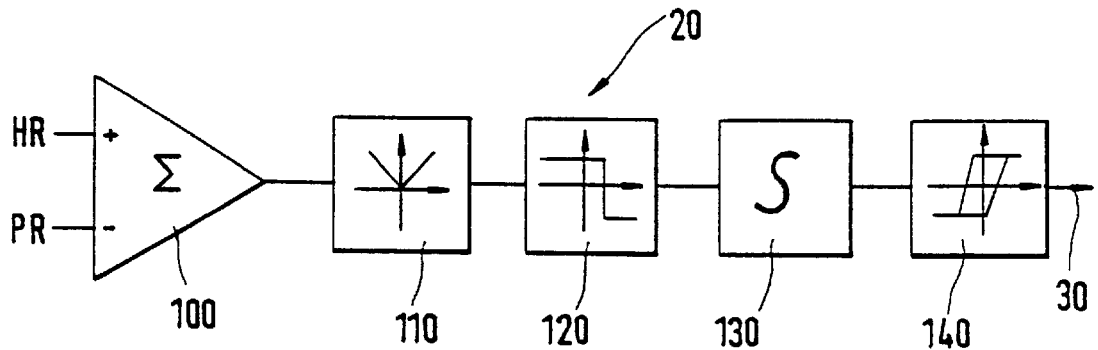
FIG. 3 shows a preferred embodiment of the coincidence detection unit.

FIG. 3 shows a preferred embodiment of the coincidence detection unit 20. The heart rate signal HR (e.g. derived from ultrasound or ECG, such as a direct scalp ECG in fetal monitoring) is fed to a first (e.g. positive) input terminal of a summing circuit 100 and the pulse rate PR (derived from pulse oximetry) is fed to a second (e.g. negative) terminal thereof. The summing circuit 100 generates a difference signal on an output terminal thereof indicative of the difference between the heart rate HR and the pulse rate PR. The difference signal is fed to an absolute value generator 110 that produces the absolute value of the provided difference signal.

A threshold comparator 120 compares the absolute value of the difference signal, derived from the absolute value generator 110, with a predetermined limit and outputs e.g. a positive constant if the absolute value is below the limit. Correspondingly, a negative constant is output if the absolute value is above the limit. It is to be understood that the threshold limit can also be an adaptive limit and that the output signal of the threshold comparator 120 can be a variable value instead of a constant value. This allows giving the output signal of the threshold comparator 120 a weighting dependent on the absolute value of the heart rate HR and the difference value between the heart rate HR and the pulse rate PR.

The output of the threshold comparator 120 is summed up by an integrator circuit 130. The integrator circuit 130 provides a built-in limitation function that avoids an overflow if the input signal is positive for a long period of time or an underflow if it is negative.

A second threshold comparator 140 compares the output signal from the integrator circuit 130 with one or more thresholds and outputs a first (e.g. positive) signal if the integration output is above a predetermined or adaptive limit. Correspondingly, a second (e.g. negative) signal is output if the integration output is below a predetermined or adaptive limit. Preferably, the second threshold comparator 140 has a built-in hysteresis to avoid a fast changing output if the output of the integrator circuit 130 is permanently changing around the threshold values of the second comparator 140.

The second threshold comparator 140 preferably provides a positive output when the heart rate HR and the pulse rate PR are within a certain range. A negative output is provided when the heart rate HR and the pulse rate PR are not within the given range.

When the output of the second threshold comparator 140 is negative, the heart rate HR, derived e.g. from ultrasound or ECG, and the pulse rate PR, derived from pulse oximetry, are different, thus indicating that the sources of the heart rate HR and the pulse rate PR are probably not the same. This can be the case, e.g. in fetal monitoring, when the pulse rate PR is derived from maternal pulses instead of from fetal pulses, or if a fetal arrhythmia is present.

When the output of the second threshold comparator 140 is negative, thus indicating a mismatch between the pulse rate PR and the heart rate HR, a warning signal is preferably generated indicating to a user to check the measurement conditions and to reposition or to replace a pulse oximetry sensor, if required. Typically the values of the heart rate HR derived by ultrasound or by direct scalp ECG measurements are more accurate and reliable than e.g. optically derived pulse rates PR from pulse oximetry. In addition, during fetal and/or maternal movements, the $SpO_2$ pulse signals can be influenced by those movements, so that wrong pulse rates PR could by delivered. In these cases, the warning given to the user might help to make a better interpretation of the measurement result, thus improving patient management.

The coincidence evaluation unit 40 can be embodied by any hardware or software means known in the art.

In a preferred embodiment, the coincidence detection according to the invention is implemented using digital components and an integrated microprocessor. However, analog or partly analog implementations are possible accordingly.

Further embodiments for the coincidence detection according to the invention, and in particular for the coincidence detection unit 20, can be derived from U.S. Pat. No. 5,123,420 by replacing HR1 by the pulse rate PR and HR2 by the heart rate HR, or vice versa. In particular, the various coincidence detection methods and apparatuses described in FIGS. 2–4, 6–7, 8–9, and 10 plus corresponding parts of the description of U.S. Pat. No. 5,123,420 are applicable for the purpose of the present invention and shall be incorporated herein by reference.

What is claimed is:

1. A signal matching recognition unit receiving a first signal indicative of a pulse rate derived from pulse oximetry and a second signal, indicative of a heart rate, that is derived from a technique other than pulse oximetry, the signal matching recognition unit comprising:
   a signal matching detection unit for generating a third signal indicative of a signal match between the first signal and the second signal.

2. The signal matching recognition unit of claim 1, further comprising:
   a signal matching evaluation unit receiving the third signal for generating therefrom a fourth signal when the third signal exceeds a predefined relation to a given limit.

3. The signal matching recognition unit of claim 1, wherein the signal matching detection unit comprises means for determining a signal match between the first signal and the second signal.

4. The signal matching recognition unit of claim 1, wherein the signal matching detection unit comprises:
   a summing circuit, receiving the first signal and the second signal, for generating a difference signal indicative of the difference between the first signal (PR) and the second signal (HR),
   a first comparator for comparing the difference signal with a predetermined limit and for providing an output corresponding the difference signal,
   an integrator circuit for summing up the output received from the first comparator, and
   a second comparator for comparing a signal provided by the integrator circuit with one or more threshold values and for providing the third signal.

5. The signal matching recognition unit of claim 4, wherein the signal matching detection unit further comprises an absolute value generator, receiving the difference signal, for generating the absolute value of the difference signal, whereby the first comparator receives and compares the absolute value of the difference signal with a predetermined limit and provides an output corresponding the received absolute value of the difference signal.

6. A pulse oximetry unit comprising:
   a pulse oximeter generating a first signal indicative of a pulse rate,
   a heart rate determination unit generating a second signal, indicative of a heart rate, that is derived from a technique other than pulse oximetry, and
   a signal matching recognition unit wherein said signal matching recognition unit receives the first signal from the pulse oximeter and the second signal from the heart rate determination unit and provides a third signal indicative of the signal matching between the first signal and the second signal to the pulse oximeter for validating the accuracy of measured oxygen saturation values.

7. The pulse oximetry unit of claim 6, wherein the signal matching recognition unit provides a warning signal to the pulse oximeter, indicating that the oxygen saturation value is not sufficiently accurate and/or invalid, when the signal matching recognition unit recognizes a mismatch between the pulse rate and the heart rate.

8. A method for validating the accuracy of oxygen saturation values measured by a pulse oximeter, comprising the steps of:
   (a) receiving a first signal indicative of a pulse rate derived from pulse oximetry and a second signal, indicative of a heart rate, that is derived from a technique other than pulse oximetry, and
   (b) generating a third signal indicative of the signal matching between the first signal and the second signal.

9. The method of claim 8, further comprising the step of:
   (c) generating a fourth signal from the third signal when the third signal exceeds a predefined relation to a given limit.

10. The method of claim 8, further comprising the step of:
    (d) providing a warning signal to the pulse oximeter, indicating that the oxygen saturation value as measured by the pulse oximeter is not sufficiently accurate and/or invalid, when a mismatch between the pulse rate and the heart rate is recognized.

* * * * *